US007403588B2

United States Patent
Bruder et al.

(10) Patent No.: US 7,403,588 B2
(45) Date of Patent: Jul. 22, 2008

(54) METHOD FOR PRODUCTION OF TOMOGRAPHIC SLICE IMAGES OF AN EXAMINATION OBJECT USING AT LEAST TWO X-RAY BEAMS AT OFFSET ANGLES, AND A COMPUTED TOMOGRAPHY SCANNER FOR CARRYING OUT THIS METHOD

(75) Inventors: Herbert Bruder, Hoechstadt (DE); Stefan Schaller, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 92 days.

(21) Appl. No.: 11/213,679

(22) Filed: Aug. 30, 2005

(65) Prior Publication Data

US 2006/0045235 A1  Mar. 2, 2006

(30) Foreign Application Priority Data

Aug. 31, 2004 (DE) ........................ 10 2004 042 491

(51) Int. Cl.
*H05G 1/60* (2006.01)
(52) U.S. Cl. ............................................. 378/9; 378/4
(58) Field of Classification Search ............... 378/4–20, 378/92, 95, 193, 210, 901
See application file for complete search history.

(56) References Cited

U.S. PATENT DOCUMENTS

| | | | |
|---|---|---|---|
| 5,825,842 A * | 10/1998 | Taguchi ........................ 378/15 |
| 6,421,412 B1 * | 7/2002 | Hsieh et al. ..................... 378/9 |
| 6,483,892 B1 * | 11/2002 | Wang et al. ................... 378/43 |
| 6,873,677 B2 * | 3/2005 | Kaufman ........................ 378/4 |
| 7,085,343 B2 * | 8/2006 | Shinno et al. .................. 378/9 |
| 7,187,746 B2 * | 3/2007 | Sakaguchi et al. ............. 378/8 |
| 2005/0111623 A1 | 5/2005 | Bruder et al. |
| 2005/0175143 A1 * | 8/2005 | Miyazaki et al. .............. 378/19 |
| 2006/0159220 A1 * | 7/2006 | Heuscher ........................ 378/9 |

FOREIGN PATENT DOCUMENTS

DE      103 54 214 A1     6/2005

* cited by examiner

*Primary Examiner*—Courtney Thomas
*Assistant Examiner*—Alexander H Taningco
(74) *Attorney, Agent, or Firm*—Harness, Dickey & Pierce, P.L.C.

(57) ABSTRACT

A method is disclosed for production of tomographic slice images of an examination object using a computed tomography scanner. In order to scan an examination object, at least two X-ray beams are produced, which each are at offset angles and fan out from a focus to an opposite detector and scan the examination object. The scans at least partially overlap. Detector output data which is emitted from the detector elements is measured together with physical orientation data of the beams and is converted to projection data sets. Slice images are then calculated. In order to calculate the complete slice images, data which is redundant from the measured data of the at least two X-ray beams from overlapping projection intervals is used for each complete slice image. The size of the overlap area of the projection data used from the individual X-ray beams is defined before the calculation of the slice images, in order to vary time resolution and image quality.

23 Claims, 6 Drawing Sheets

METHOD FOR PRODUCTION OF TOMOGRAPHIC SLICE IMAGES OF AN EXAMINATION OBJECT USING AT LEAST TWO X-RAY BEAMS AT OFFSET ANGLES, AND A COMPUTED TOMOGRAPHY SCANNER FOR CARRYING OUT THIS METHOD

The present application hereby claims priority under 35 U.S.C. §119 on German patent application number DE 10 2004 042 491.8 filed Aug. 31, 2004, the entire contents of which is hereby incorporated herein by reference.

FIELD

The invention generally relates to a method for production of tomographic slice images of an examination object. For example, it can generally relate to a method using a computed tomography scanner wherein: in order to scan the examination object, preferably with at least partially cyclically moving examination areas, at least two X-ray beams are produced. These are each at offset angles and fan out from a focus to an opposite detector with a large number of detector elements and scan the examination object, rotating about a system axis, if required. The examination object is fed forwards continuously in the system axis direction relative to the X-ray beams and the scans at least partially overlap. Detector output data which is emitted from the detector elements and represents the attenuation of the beams as they pass through the examination object is measured together with direct or indirect physical orientation data of the beams and is converted to projection data sets. The projection data sets of the at least two scanning X-ray beams are then used to calculate slice images, wherein data from a sum of scans with a projection interval of at least 180° is used for each complete slice image and includes the measurement data from the at least two scanning X-ray beams.

BACKGROUND

A computed tomography method and a corresponding computed tomography scanner for production of slice images with the aid of a plurality of X-ray beams at offset angles are generally known. In this context reference should be made in particular to the Laid-Open Specifications with the file references DE 103 54 900.5 (US 2005-0111623 A1) and DE 103 54 214 A1. The entire disclosure content of each of these laid open specifications are hereby incorporated herein by reference and are included in this description.

Both of the laid-open specifications mentioned above describe a method for reconstruction of tomographic slice images using detector data which is produced by at least two X-ray beams which are offset at an angle to one another and rotate with one another. In the first mentioned laid-open specification, complete 180° projection segments are produced from the detector data which is obtained by the two X-ray beams, can be associated with specific cycle phases of the scanned object, and can then be reconstructed to form slice image sequences. In the last-mentioned laid-open specification, it is proposed that image elements first of all be produced from small subsegments, which are combined with the correct timings to form segment image stacks, which are then added on a complementary angle-basis and in layers to form tomography slice images, which are produced from 180° segments overall.

Both methods have the common feature that, in total, data from a scanning interval of at least 180° overall is used to calculate the image from the detector data which is obtained by scanning with the aid of the at least two X-ray beams, with data from the detectors in each case being compiled with the correct angle and being used to achieve the optimum time resolution. In order to achieve the maximum time resolution, data which has been scanned over an angle of 90° is used from each X-ray beam, in the case of a computed tomography scanner with two X-ray beams offset through 90°.

By way of example, this type of scanning and the subsequent image production process make it possible to produce cardioimage sequences whose time resolution is sufficient to achieve diagnostically sufficiently relevant image statements, for example with respect to the coronaries, for a patient's heart which is beating at a normal speed. However, one problem which may occur in this case is that, in poor circumstances, the dose required to produce an effective image for diagnosis may not be sufficient for the best time resolution.

SUMMARY

An object of at least one embodiment of the invention is to find a method and/or a computed tomography scanner for carrying out the method which make it possible to improve or even optimize the image quality of a CT scan, optionally with regard to the image noise that occurs or with regard to the time resolution.

The inventors have found that, subject to certain preconditions, a sufficiently low movement frequency or speed of the object being examined may be better, in order to assess the recorded object to produce the images to be reconstructed by way of partially redundantly available detector data at the expense of the optimum time resolution, thus increasing the dose used per image and hence improving the image quality. According to at least one embodiment of the invention, the user of a computed tomography scanner is thus provided with an adjustment capability, by which he can indicate the extent to which overlapping data sets are used for the reconstruction of slice image sequences, in which case, in contrast to the normal approach, a reduction in the time resolution of the slice image sequences is accepted.

On this basis, the inventors propose that the method, for production of tomographic slice images of an examination object using a computed tomography scanner wherein in order to scan an examination object, preferably with at least partially cyclically moving examination areas, at least two X-ray beams are produced, which are each at offset angles and fan out from a focus to an opposite detector with a large number of detector elements and scan the examination object, rotating about a system axis, if required, the examination object is fed forwards continuously in the system axis direction relative to the X-ray beams and the scans at least partially overlap, detector output data which is emitted from the detector elements and represents the attenuation of the beams as they pass through the examination object is measured together with direct or indirect physical orientation data of the beams and is converted to projection data sets, the projection data sets of the at least two scanning X-ray beams are then used to calculate slice images, wherein data from a sum of scans with a projection interval of at least 180° is used for each complete slice image and comprises the measurement data from the at least two scanning X-ray beams, be improved. The method in at least one embodiment may be improved in that in order to calculate the complete slice images, data which is redundant from the measured data of the at least two X-ray beams from overlapping projection intervals is used for each complete slice image. The size of the overlap area of the projection data that is used from the individual X-ray beams may be defined before the calculation of the slice images, in order to vary time resolution and image quality.

This now provides the user of a computed tomography scanner which has at least two X-ray beams at offset angles with the capability to specify, before the calculation, the magnitude, by way of example, of the percentage of the data which will be used in a redundant form for the calculation of the computed-tomographic images. In this case, this therefore increases the dose used per reconstructed slice image, thus making it possible to achieve an improved representation of the examination object in accordance with the relationships, which are known per se, between the dose that is used for image production and the image quality.

In this case, however, one precondition is that this gain in improved image quality is not negated, in contrast, at the expense of movement fuzziness. The assessment of this is left to the user of the method, although it is normally possible, in the case of a cardioscan by way of example, to record specific areas of the heart with increased time resolution, whereas other areas which may move to a lesser extent and therefore do not necessarily require the high resolution are displayed using reconstruction methods which use an increased X-ray dose for the production of the images.

In order to avoid imaging artifacts when using redundant detector data, it is additionally proposed that the redundant data in the overlap area of the projection data be weighted with a weighting function such that the redundancy which results from the multiple measurement of the same object area by the at least two X-ray beams is compensated for.

By way of example, the weighting function can be used to uniformly weight each component of the measurement values from n X-ray beams with 1/n throughout the entire overlap area. However, this procedure may lead to the probability of artifacts being created in the transitional areas between the overlap area and the area which is not overlapped.

In order to reduce or even avoid these artifacts, the inventors additionally propose that the weighting function in the majority of the overlap area uniformly weights each component of the measurement values from n X-ray beams with 1/n, wherein there is a continuous rise in the weighting of the next X-ray beam in the revolution direction in the boundary area of the overlaps. Further, the sum of the weightings may be normalized overall, that is to say it remains equal to 1.

In the described method of at least one embodiment, it is possible on the one hand that before the reconstruction process, weighted projection data sets are produced with a projection interval of at least 180°, and complete slice images are produced from them. Fundamentally, this corresponds to the method as described in the laid-open specification with the file reference DE10354900.5, the entire contents of which are incorporated herein by reference.

On the other hand, it is also possible by using the method according to at least one embodiment of the invention for the reconstruction process, to produce incomplete image elements from the data sets of the individual X-ray beams with a projection interval of less than 180°, which are weighted in order to produce complete slice images corresponding to the amount of overlap. This method corresponds to the reconstruction method described in the laid-open specification with the file reference DE10354214.0, the entire contents of which are incorporated herein by reference.

With respect to the X-ray beams which are used, it is preferably possible to use two, and only two, X-ray beams which are at offset angles to one another and are preferably arranged at right angles to one another. X-ray beams such as these may not only be of the same size but may also be equipped with different fan angles.

As an alternative to this, it is also possible to use three X-ray beams which are at offset angles to one another and are preferably offset through 60° or 120°. Once again, these X-ray beams may either be designed to be identical or may be provided with different fan angles.

The described method at least one embodiment can be used not only for a 2D reconstruction method but also for a 3D reconstruction method, in which the reconstruction is produced on a voxel basis.

Furthermore, the inventors propose that the method of at least one embodiment be designed such that a different overlap size is individually entered by the operator immediately before the calculation of the CT images, in which case the calculation can preferably be carried out repeatedly using the same measured detector output data during a scan with at least two X-ray beams, with a plurality of image sequences being produced which differ by the use of projection intervals with overlaps of different size.

This procedure allows the operator to decide from analysis of a calculated image sequence whether he will accept higher or lower time resolution in order in each case to obtain a better image quality on the basis of the greater dose that is used.

In a corresponding manner to the idea of the inventors as described above, they also propose in at least one embodiment that a computed tomography scanner, preferably a cardio CT, for production of slice image sequences of an examination object with a specific time resolution and image quality, having at least: means for production of at least two X-ray beams, which each originate from a focus in a fan shape, and rotate about a common system axis in order to scan the, preferably periodically moving, object, if required, means for movement of the examination object along the system axis, means for reconstruction of slice image sequences from detector output data which has been produced by the at least two X-ray beams, be equipped to improve it in such a way that an input apparatus is provided for the desired overlap of the detector output data used from the at least two X-ray beams, in order to calculate the slice images.

An input apparatus such as this may, for example, be a potentiometer, possibly in the form of a rotary potentiometer or slide potentiometer, or else may be an input apparatus which, as a screen/program combination, is combined with a so-called "human device interface", that is to say a keyboard, a mouse or a joystick or the like, so as to allow the desired level of overlap to be set by the operator.

In a corresponding manner to the method as described above, in at least one embodiment a computed tomography scanner such as this may have two, and only two, X-ray beams, preferably offset through 90°, or three X-ray beams, preferably offset through 60° or 120°. X-ray beams such as these may either be produced by an X-ray tube arranged in a gantry, or else it is possible to allow a previously accelerated electron beam to strike a rotating anode or an anode arranged in the form of a circle around the patient, by appropriate deflection, and thus to achieve a plurality of appropriately shaped X-ray beams. With regard to the detectors, it is possible to use both detectors of the same size and detectors of different size, which are located opposite the foci and rotate appropriately about the system axis of a CT. However, it is also within the scope of at least one embodiment of the invention to use stationary hollow-cylindrical detectors with a large number of detector elements, in which case only the X-ray beam, possibly together with an X-ray tube, rotates around the patient.

BRIEF DESCRIPTION OF THE DRAWINGS

Embodiments of the invention will be described in more detail in the following text with reference to the figures, in which the following reference symbols and variables are used: 1: CT scanner; 2: first X-ray tube; 3: first detector; 4: second X-ray tube; 5: second detector; 6: housing; 7: patient; 8: couch; 9: system axis; 10: computation unit; 10.1: potentiometer; 11: circle segment/projection data of the first detector; 11.1: weighting function of the first detector; 12: circle segments/projection data of the second detector; 12.1: weighting function of the reconstruction interval; 14.1-14.5: projection segments; 15: sum of the weighting functions; 16: overlap area; 17: boundary of the projection segments; 18: overlap boundary; $D_x$: detectors; $F_x$: foci; $L_x$: length of the detectors; $Prg_1$-$Prg_n$: program modules; $S_x$: X-ray fan; $\beta_x$: fan angle; $\gamma$: weighting function.

In detail.

DETAILED DESCRIPTION OF THE EXAMPLE EMBODIMENTS

Figure 1:
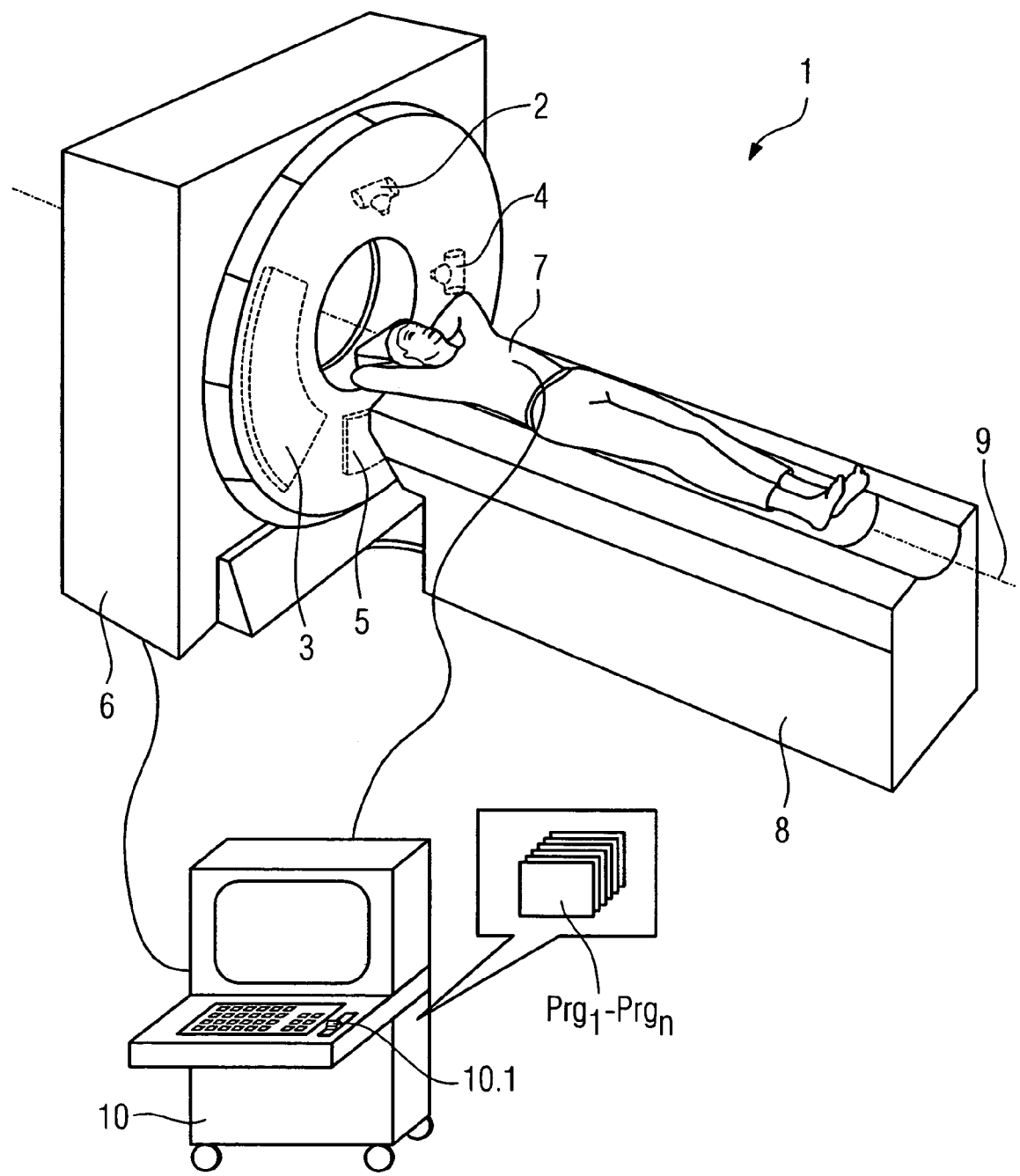
FIG. 1 shows a schematic 3D display of a cardio CT.

FIG. 1 shows a cardio CT 1 according to at least one embodiment of the invention, illustrated schematically in three dimensions. The CT includes a housing 6 in which a rotating frame (gantry), which is not illustrated explicitly, is located and with whose aid two X-ray tubes 2 and 4, together with the multiple row detectors 5 and 3, which are in each case opposite, rotate around a patient. The patient is located on a patient couch 8 which can be moved along the system axis 9.

The combination of rotation of the X-ray/detector combinations and the linear movement of the patient results, in the known manner, in a spiral scan of the patient 7. The gantry and the X-ray tubes located on it, as well as the longitudinally movable couch 8, are controlled by a computation unit 10 by processing predetermined programs $Prg_1$-$Prg_n$.

During the scan, the detectors produce detector output data which is transmitted to the computation unit 10, with the computation unit 10 also receiving ECG information from the patient at the same time, so that cardio-CT image sequences are reconstructed in a manner known per se. By way of example, a potentiometer or slide controller 10.1, by which it is possible to set the overlap according to at least one embodiment of the invention of the projection intervals that are used, is located on the computation unit 10.

Figure 2:
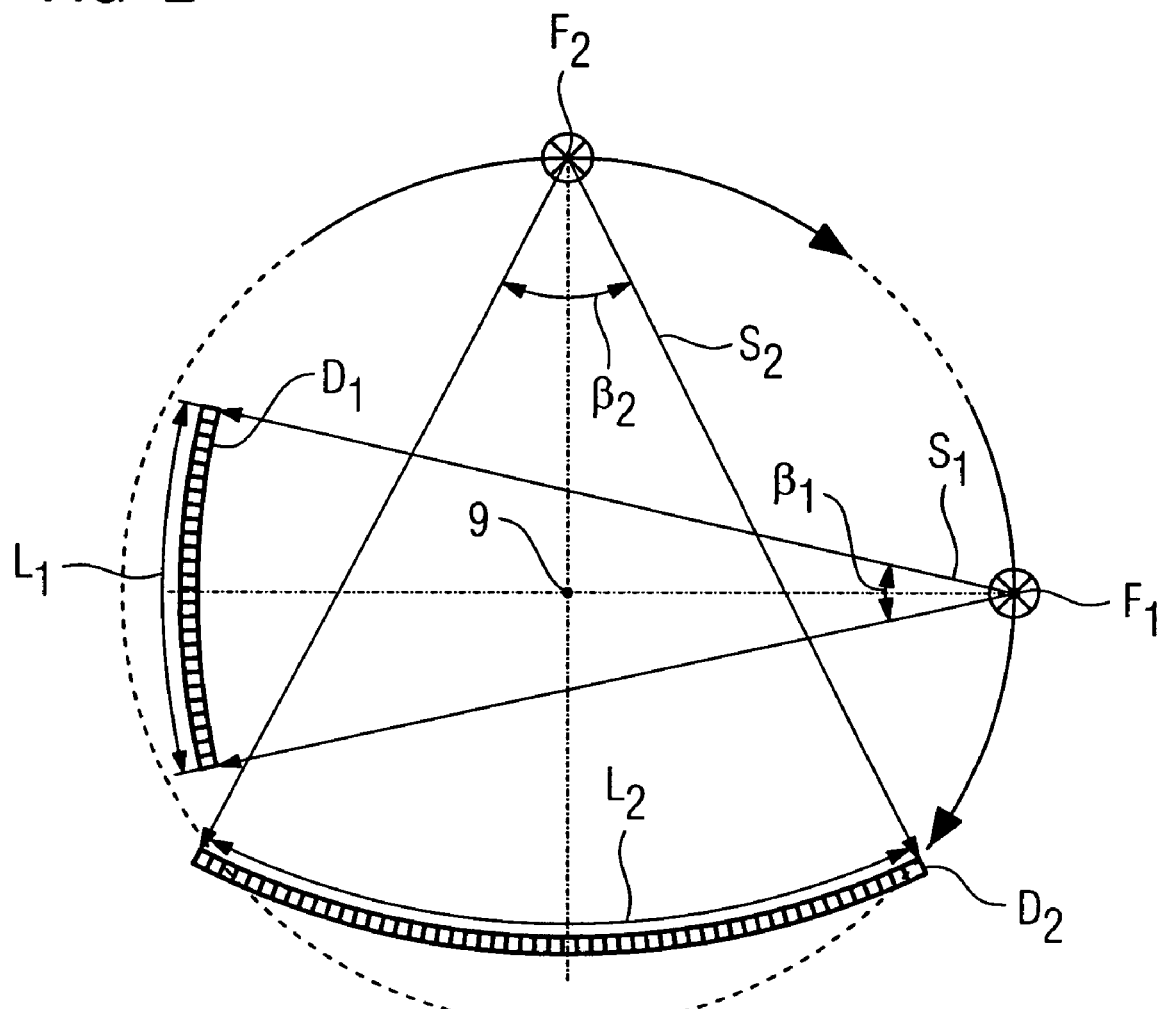
FIG. 2 shows a section through a gantry with two foci and two detectors of different size.
Figure 3:
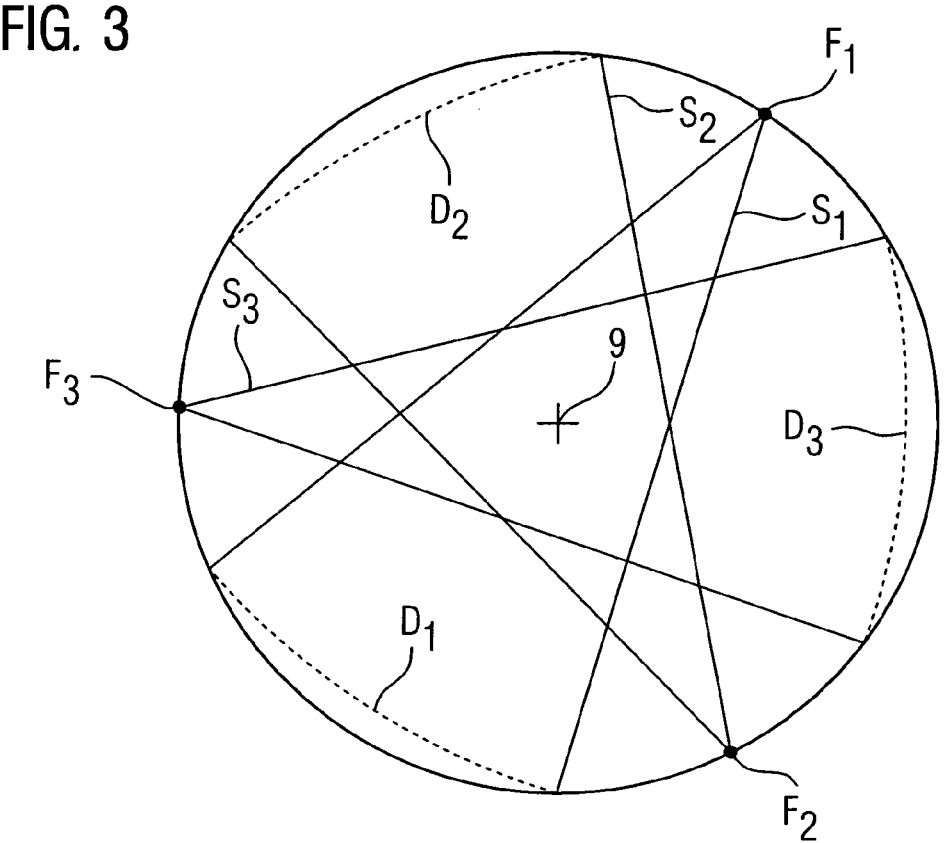
FIG. 3 shows a schematic example of a CT with 3 X-ray beams at offset angles.
Figure 4:
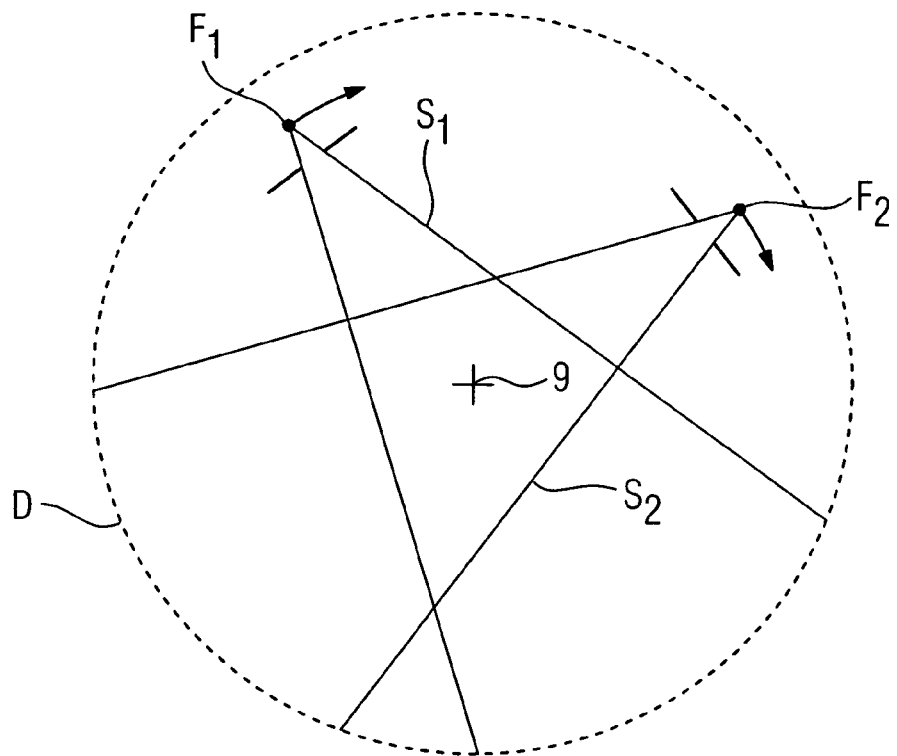
FIG. 4 shows a schematic example of a CT with two X-ray beams at offset angles and with a detector covering 360°.

Once again schematically, FIGS. 2, 3 and 4 show different variations of focus/detector combinations which are suitable for carrying out the method according to at least one embodiment of the invention.

FIG. 2 shows two different multiple row detectors, in the form of a cross slice. The detector $D_1$ has a considerably shorter length $L_1$ than the detector $D_2$, whose length is $L_2$. In a corresponding manner, the X-ray fans $S_1$ and $S_2$, which respectively extend from the focus $F_1$ and the detector $D_1$ and from the focus $F_2$ to the detector $D_2$ have fan angles $\beta_1$ and $\beta_2$ of different size. The X-ray beams are in this case at right angles to one another—with respect to their center lines, that are shown by dashed-dotted lines.

FIG. 3 shows another variant of three focus/detector combinations with three foci $F_1$, $F_2$ and $F_3$, which are located opposite respective detectors $D_1$ to $D_3$, which are arranged on a gantry, with the associated X-ray fans $S_1$ to $S_3$ being arranged offset through an angle of 120° with respect to their center lines, which are not illustrated here.

Finally, FIG. 4 also shows an additional possible variant of focus/detector combinations. This shows a detector D which is arranged in an annular shape and which, in contrast, does not rotate with respect to the two illustrated foci $F_1$ and $F_2$. Only the X-ray sources which form the foci $F_1$ and $F_2$ rotate during the scan around a centrally arranged examination object, and in the process each form an X-ray fan $S_1$ and $S_2$. The X-ray fans are offset through an angle of 90° with respect to one another in a similar manner to that shown in FIG. 2, and produce detector signals on the detector D, which is arranged like a hollow cylinder, by which it is possible to scan the absorption values for the examination object through which the X-ray beam has passed.

All of the illustrated focus/detector variants, which are intended to illustrate only a selection of possible embodiments, are shown with at least two X-ray beams, which scan an examination object while rotating about a system axis and in the process correspondingly produce detector output data. According to at least one embodiment of the invention, this output data is used with an overlap size, which can be determined by the operator, to produce CT slice images, as illustrated by way of example in FIG. 5.

Figure 5:
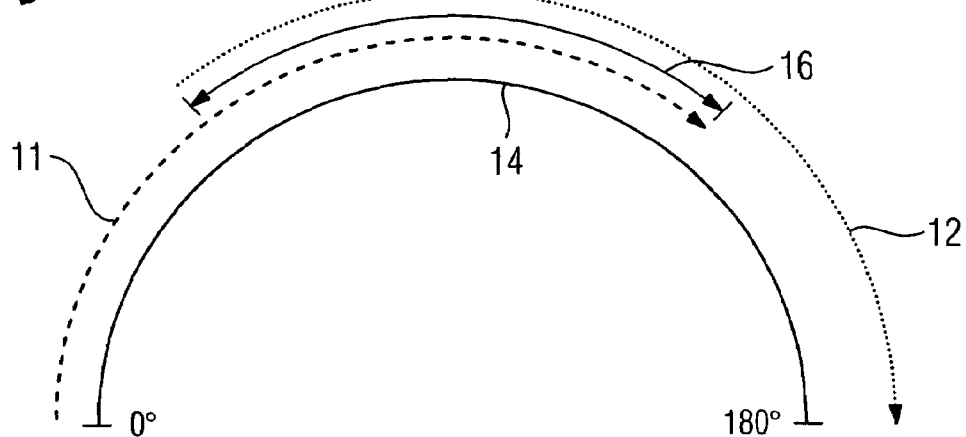
FIG. 5 shows an illustration of the overlapping data used for image reconstruction from two X-ray beams at offset angles.

FIG. 5 shows, schematically, the scanning of an examination object over a total angle of 180° overall, with a total of two X-ray beams at offset angles. It should expressly be noted that the illustration shown is not intended to represent the actually scanned projection angles of the two X-ray beams, but that FIG. 5 illustrates only the size of the overlap zone of the data that is used for the subsequent image reconstruction and originates from the respective detectors. The data from the detector $D_1$ corresponds to the circle segment 11, while the data from the detector $D_2$ corresponds to the circle segment 12. The overlap zone is represented by the circle segment 16. In the end, a projection interval of 180°—as is intended to be illustrated by the circle segment 14—is produced by combination of the two sets of data and taking account of the appropriate weighting.

Figure 6:
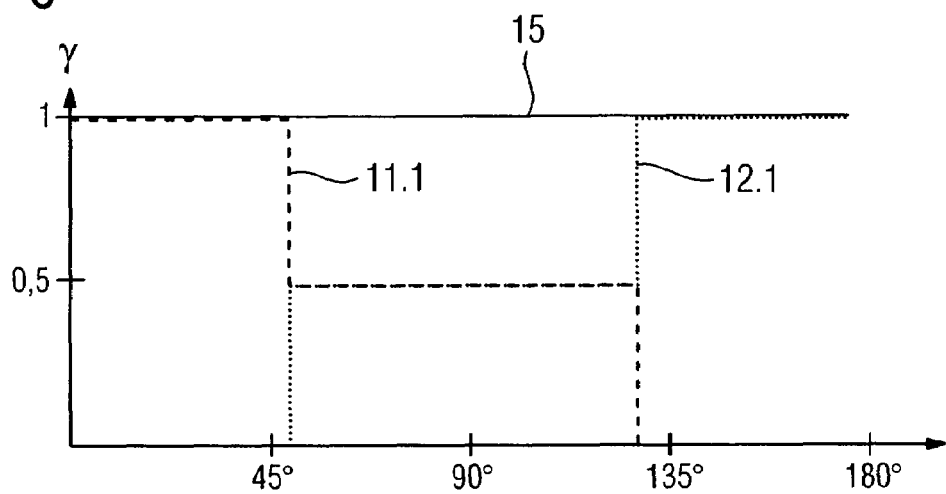
FIG. 6 shows a first example of the profile of the weighting function plotted against the reconstruction interval from FIG. 5.

FIG. 6, below this, in this case shows the associated weighting function γ of the data from the two detectors plotted against the projection angle of 180°. In this case, the weighting function 11.1 is allocated to the data from the first detector $D_1$, corresponding to the circle segment 11, and the profile of the weighting function 12.1 is allocated to the data from the second detector $D_2$, corresponding to the circle segment 12.

Overall, the sum of the weighting functions—represented by the line 15—over the entire projection angle range of 180° is always 1. A weighting function of 1 is used in a corresponding manner in the angle ranges which are covered only by data from one detector, and a weighting function of 0.5 is used for the data from both detectors in each case in the overlapping areas.

However, it should expressly be noted that the two detectors do not necessarily always need to have the same weighting. It is thus possible, for example, to take account of different detector qualities by distributing the weightings nonuniformly between the detectors.

Figure 7:
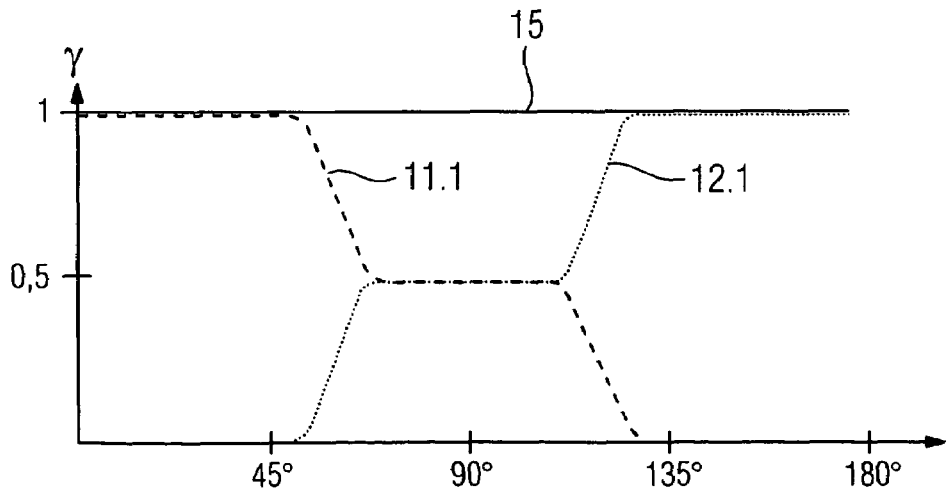
FIG. 7 shows a second example of the profile of the weighting function plotted against the reconstruction interval from FIG. 5.

FIG. 7 shows another example of the profile of the weighting functions, similar to that shown in FIG. 6, in this case, however, illustrating the transition between the non-overlap and overlap areas smoothly, so that it is possible to avoid artifacts resulting from a sharp transition—as illustrated in FIG. 6.

Figure 8:
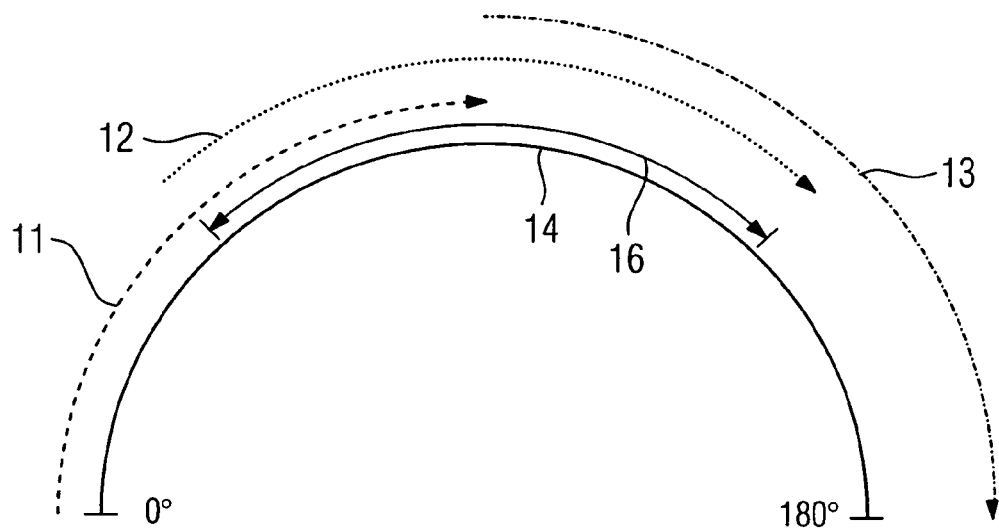
FIG. 8 shows an illustration of the overlapping data used for image reconstruction from three X-ray beams at offset angles.

FIG. 8 shows—in a similar way to FIG. 5—a reconstruction interval 14 over 180° once again, but in this case using data from a total of three detectors in order to form the reconstruction interval, with an overlap area 16 once again being created here using respectively redundant data from two detectors to form the reconstruction interval 14. Data sets such as these may originate, for example, from focus/detector combinations as illustrated in FIG. 3.

Figure 9:
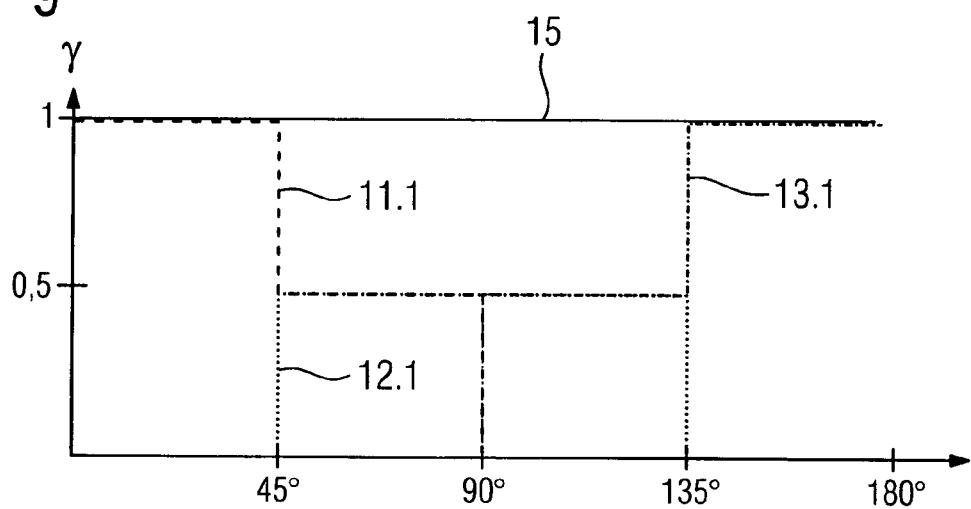
FIG. 9 shows a first example of the profile of the weighting function plotted against the reconstruction interval from FIG. 8.
Figure 10:
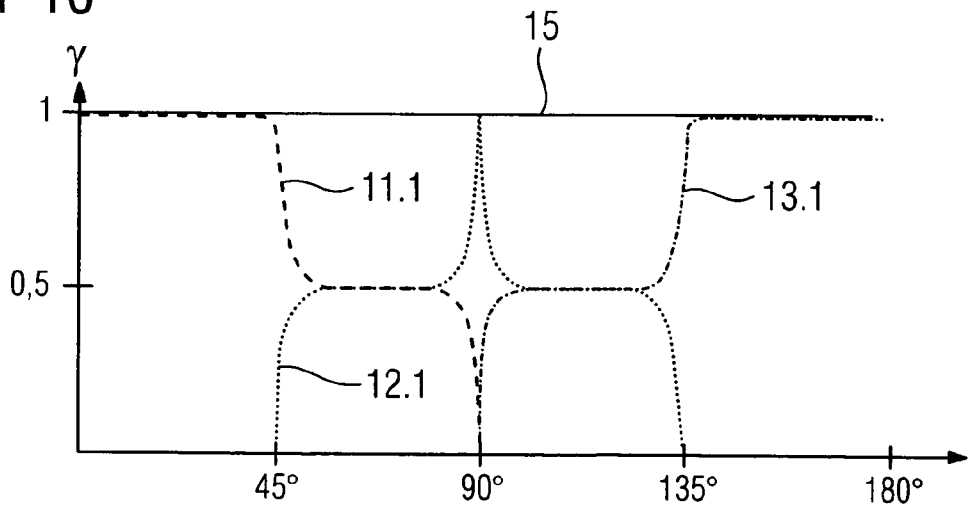
FIG. 10 shows a second example of the profile of the weighting function plotted against the reconstruction interval from FIG. 8.

FIGS. 9 and 10 show examples of some of the profile of weighting functions γ which can be used here. The profile of the weighting function 11.1 for the projection data 11 from the first detector in both FIGS. 9 and 10 remains at the value 1 in the range between 0 and 45°, falls to 0.5 between 45 and 90°, and does not exist between 90 and 180°. The weighting function 12.1 for the projection data 12 from the second detector has the value 0 from 0 to 45°, then rises to the value 0.5 until an angle of 135°, and then falls back to 0 again. The weighting function 13.1 for the data from the third detector starts with the value 0.5 at 90°, rises to the value 1 after 135°, and remains at this value until 180°. FIG. 9 shows sudden transitions between the different weighting values.

The sum of all the weighting functions is represented by the line 15, and is 1 over the entire projection interval.

The profile of the weighting function in FIG. 10 is fundamentally the same, but a softer transition between the individual areas is also shown here, in order to avoid image artifacts. In this case, it is worth noting that the weighting function 12.1 of the second detector rises briefly to the value 1 in the region of 90°, in order to allow a smooth transition to the other weighting functions.

In this case, it should also be noted that the weighting functions in the overlap area need not necessarily have the same value for both overlapping detectors. In this case as well, it is possible for a better-quality detector to have a higher weighting than a detector of poorer quality.

In addition, it should be noted that the illustrated variants, in which overlaps in which in each case only two detectors overlap are shown, are only exemplary. It is also possible without any problems to additionally find reconstruction intervals in which the values from three detectors overlap so that, in this case, the redundancy of the data from a total of three detectors is taken into account for a specific projection range, by the use of an appropriate weighting function.

The examples illustrated in FIGS. 5 to 10 of the production of projection intervals may be used for all reconstruction methods in which 180° projection intervals are used overall for reconstruction. However, if image calculation methods are used which carry out their reconstruction of image elements initially with the aid of incomplete reconstruction intervals of less than 180°, and then assemble the reconstructed image elements to form oval images, then the described method can be transferred to these segment elements. Two such examples are illustrated in FIGS. 11 and 12.

Figure 11:
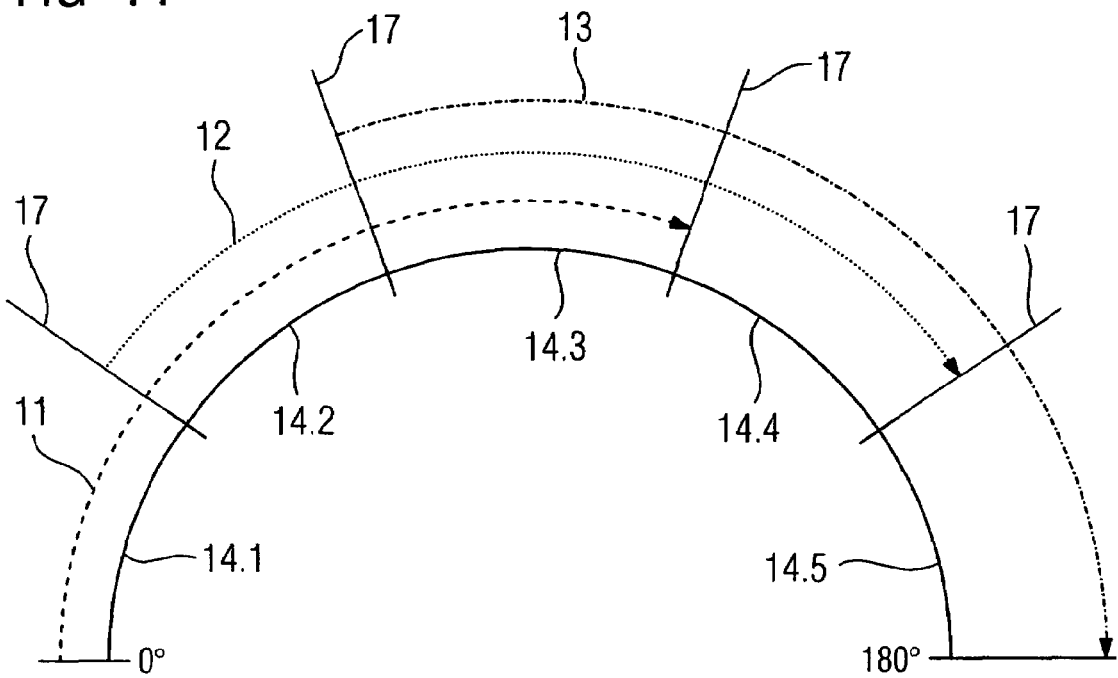
FIG. 11 shows an example of the use of the data from three overlapping detector data items with identical overlap and segment boundaries for the segmented reconstruction of incomplete image elements.

FIG. 11 shows a simple variant of at least one embodiment of the method. In this case, the data from a system with three focus/detector combinations, which correspondingly produce three X-ray beams, is processed, with the detector data from the first, second and third X-ray beams once again being annotated with the reference numbers 11, 12 and 13. In this case, the reconstruction interval from 0 to 180° is subdivided into five equal projection segments 14.1 to 14.5, with the segment boundaries advantageously matching the overlap boundaries of the detector data, so that it is possible to use a constant weighting for the detector data over the entire length of a projection segment 14.1 to 14.5.

In the illustrated example, the projection segment 14.1 has exclusively projection data 11 originating from the first X-ray beam. The projection segment 14.2 has exclusively projection data 11 and 12 from the first and second X-ray beams from the start to the end, which are in each case weighted 50:50 or corresponding to their detector quality. The central projection segment 14.3 has projection data from all three X-ray beams, and from the associated detectors $D_1$-$D_3$, which are each weighted with a weighting function of γ equal to ⅓, if the detector quality is the same. Once again, the projection segment 14.4 contains data only from the second and third X-ray beams, while the last projection segment 14.5 contains only the projection data 13 from the third X-ray beam. These reconstruction intervals 14.1 to 14.5 are then used to calculate incomplete image elements, as is described in the laid-open specification cited above with the official file reference DE10354214.0, and being assembled to form complete slice images.

Figure 12:
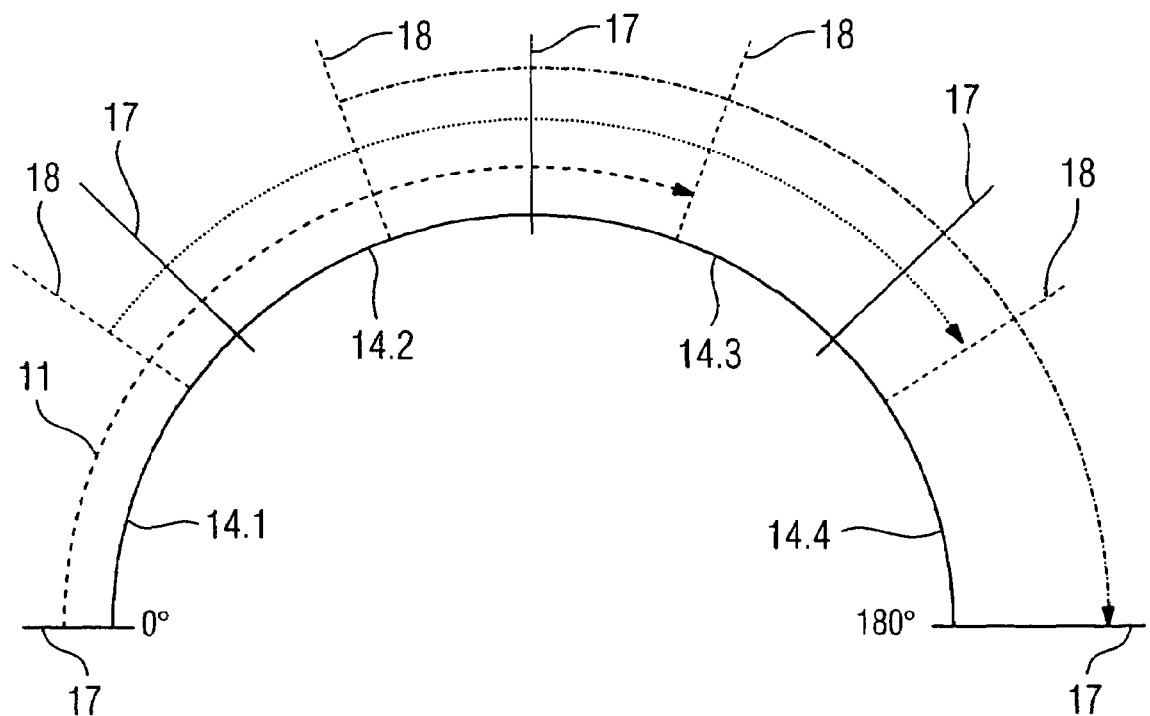
FIG. 12 shows an example of the use of the data from three overlapping detector data items with unequal overlap and segment boundaries for the segmented reconstruction of incomplete image elements.

FIG. 12 shows a more difficult situation in terms of the production of the projection segment elements, since the boundaries 17 of the projection segments 14.1 to 14.4 illustrated there no longer coincide with the overlap boundaries 18 of the projection data of the individual X-ray beams. However, in this case, it is possible to use a similar calculation rule—to that which is used for an overall projection segment from 0 to 180° corresponding to FIG. 5 or 8—so that those segments in which the projection data from a number of X-ray beams partially overlaps can be evaluated appropriately.

In this case as well, it is, of course, also possible to use smooth transitions in the weighting functions at the overlap boundaries, in order to avoid image artifacts.

Thus, overall, at least one embodiment of the invention provides a method for production of tomographic slice images which allows the user of a corresponding computed tomography scanner to set the time resolution and the dose used for calculation of the slice images in a variable manner, and thus to set an improved or even optimum image quality for identification of individual structures in the examination object.

In this case, it should expressly be noted that the described method can be used not only in the field of cardio-CT examination but also for the examination of any desired moving examination objects. In the case of cardio-CT examinations, additional ECG information is generally used in order to make it possible to combine data from a number of cycles with the correct timings. A corresponding situation applies to other cyclically moving examination objects. However, in at least one embodiment the method can also be used for generally moving examination objects, for whose 3D representation by means of image sequences it is intended to use different time resolutions and, corresponding to this, different dose amounts for image production, in a variable manner.

In addition, it should also expressly be noted that the method according to at least one embodiment of the invention can be used both for a spiral scan and for a circular scan.

It is self-evident that the features of the embodiments of the invention that have been mentioned above can be used not only in the respectively stated combination, but also in other combinations or on their own, without departing from the scope of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for production of tomographic slice images of an examination object using a computed tomography scanner, comprising:
    scanning an examination object using at least two X-ray beams, the beams being at offset angles and fanning out from a focus to an opposite detector with a large number of detector elements, with rotational scans at least partially overlapping in a rotational direction,
    measuring detector output data from the detector elements, representing attenuation of the beams passing through the examination object, together with direct or indirect physical orientation data of the beams and converting the data to projection data sets;
    calculating image slices, from the projection data sets of the at least two scanning X-ray beams; wherein
        data from a sum of scans with a projection interval of at least 180° is used for each complete slice image and includes the measurement data from the at least two scanning X-ray beams, and wherein
        in order to calculate the complete slice images, data redundant from the measured data of the at least two X-ray beams from rotationally overlapping projection intervals is used for each complete slice image, the size of the overlap area of the projection data used from the individual X-ray beams being defined before the calculation of the slice images, to vary time resolution and image quality; and
    displaying visible picture data based on the calculated image slices.

2. The method as claimed in claim 1, wherein, in the overlap area of the projection data, the redundant data is weighted with a weighting function, such that the redundancy which results from the multiple measurement of the same object area by the at least two X-ray beams is compensated for.

3. The method as claimed in claim 2, wherein the weighting function throughout the entire overlap area uniformly weights each component of the measurement values from n X-ray beams with 1/n.

4. The method as claimed in claim 2, wherein the weighting function in the majority of the overlap area uniformly weights each component of the measurement values from n X-ray beams with 1/n, and wherein there is a continuous rise in the weighting of the next X-ray beam in the revolution direction in the boundary area of the overlaps, with the sum of the weightings being 1.

5. The method as claimed in claim 1, wherein, before the reconstruction process, weighted projection data sets are produced with a projection interval of at least 180°, and complete slice images are reconstructed from them.

6. The method as claimed in claim 1, wherein, during the reconstruction process, incomplete image elements are produced from the data sets of the individual X-ray beams with a projection interval of less than 180°, and are weighted in order to produce complete slice images corresponding to the amount of overlap.

7. The method as claimed in claim 1, wherein two, and only two, X-ray beams are used, which are at offset angles to one another.

8. The method as claimed in claim 1, wherein three, and only three, X-ray beams are used, which are at offset angles to one another.

9. The method as claimed in claim 1, wherein the reconstructions are produced on a voxel basis.

10. The method as claimed in claim 1, wherein a different overlap size is entered by the operator immediately before the calculation of the CT images.

11. The method as claimed in claim 10, wherein a plurality of slice image sequences are produced using the same measured detector output data during a scan with the at least two X-ray beams, and differ by the use of projection intervals with overlaps of different size.

12. The method of claim 1, wherein the beams are produced to scan at least partially cyclically moving examination areas.

13. The method as claimed in claim 1, wherein two, and only two, X-ray beams are used, which are arranged at right angles to one another.

14. The method as claimed in claim 1, wherein three, and only three, X-ray beams are used, which are offset through 60° or 120°.

15. A computed tomography scanner for production of slice image sequences of an examination object, comprising:
    means for production of at least two X-ray beams, each originating from a focus in a fan shape and for rotating about a common system axis in order to scan the object;
    means for reconstruction of slice image sequences from detector output data produced by the at least two X-ray beams;
    an input apparatus, provided for a desired rotational overlap of the detector output data used from the at least two X-ray beams, in order to calculate the slice images; and
    means for displaying visible picture data based on the calculated image slices.

16. The computed tomography scanner as claimed in claim 15, wherein the input apparatus is a potentiometer.

17. The computed tomography scanner as claimed in claim 15, wherein the input apparatus is a screen and program combination with a human device interface, thus making it possible to set the desired degree of overlap.

18. The computed tomography scanner as claimed in claim 15, wherein two, and only two, X-ray beams are provided.

19. The computed tomography scanner as claimed in claim 15, wherein three, and only three, X-ray beams are provided.

20. The computed tomography scanner of claim 15, wherein the computed tomography scanner is a cardio CT.

21. The computed tomography scanner as claimed in claim 15, wherein two, and only two, X-ray beams are provided, offset through 90°.

22. The computed tomography scanner as claimed in claim 15, wherein three, and only three, X-ray beams are provided, offset through 60° or 120°.

23. A computed tomography scanner for production of slice image sequences of an examination object, comprising:
means for scanning an examination object using at least two X-ray beams, the beams being at offset angles and fanning out from a focus to an opposite detector with a large number of detector elements, with rotational scans at least partially overlapping in a rotational direction,
means for measuring detector output data from the detector elements, representing attenuation of the beams passing through the examination object, together with direct or indirect physical orientation data of the beams and converting the data to projection data sets;
means for calculating image slices, from the projection data sets of the at least two scanning X-ray beams; and
means for displaying visible picture data based on the calculated image slices; wherein
data from a sum of scans with a projection interval of at least 180° is used for each complete slice image and includes the measurement data from the at least two scanning X-ray beams, and wherein
in order to calculate the complete slice images, data redundant from the measured data of the at least two X-ray beams from rotationally overlapping projection intervals is used for each complete slice image, the size of the overlap area of the projection data used from the individual X-ray beams being defined before the calculation of the slice images, to vary time resolution and image quality.

* * * * *